United States Patent [19]
Stetter et al.

[11] Patent Number: 5,315,673
[45] Date of Patent: May 24, 1994

[54] OPTICAL WAVEGUIDE VAPOR SENSOR

[75] Inventors: Joseph R. Stetter, Naperville; G. Jordan Maclay, Maywood; David S. Ballantine, Jr., DeKalb, all of Ill.

[73] Assignee: Transducer Research, Inc., Naperville, Ill.

[21] Appl. No.: 848,240

[22] Filed: Mar. 9, 1992

[51] Int. Cl.⁵ .............................................. G02B 6/02
[52] U.S. Cl. ...................................... 385/12; 385/145
[58] Field of Search .................. 385/12, 141, 144, 145, 385/13, 126, 127; 250/227.11, 227.14, 227.18, 227.21

[56] References Cited

U.S. PATENT DOCUMENTS

| | | | |
|---|---|---|---|
| 4,834,497 | 5/1989 | Angel | 385/12 |
| 4,846,548 | 7/1989 | Klainer | 385/12 |
| 5,045,282 | 9/1991 | Kritzman et al. | 250/227.14 |
| 5,082,632 | 1/1992 | Partin et al. | 356/38 |
| 5,094,517 | 3/1992 | Franke | 385/12 |

Primary Examiner—Rodney B. Bovernick
Assistant Examiner—John Ngo
Attorney, Agent, or Firm—Solomon Zaromb

[57] ABSTRACT

An optical waveguide sensor for the detection of acid vapors comprises a chemically sensitive reagent coating of bromothymol blue or thymol blue indicator suspended in a Nafion polymer film. The sensor uses a 562-nm light-emitting diode source and a phototransistor detector. The response to HCl and $H_2S$ vapors is both rapid and reversible, with an estimated detection limit for $H_2S$ of less than 15 ppmv (parts per million by volume). The sensor exhibits generalized response to protonic acid vapors, but does not produce an indicator response to $CO_2$, even at large concentrations (60 volume-%) in the presence of water vapor. The sensor exhibits a systematic interference from water vapor which may be corrected by a differential approach, either using a reference sensor (Nafion without an indicator) or by monitoring the sensor responses at two wavelengths.

20 Claims, 14 Drawing Sheets

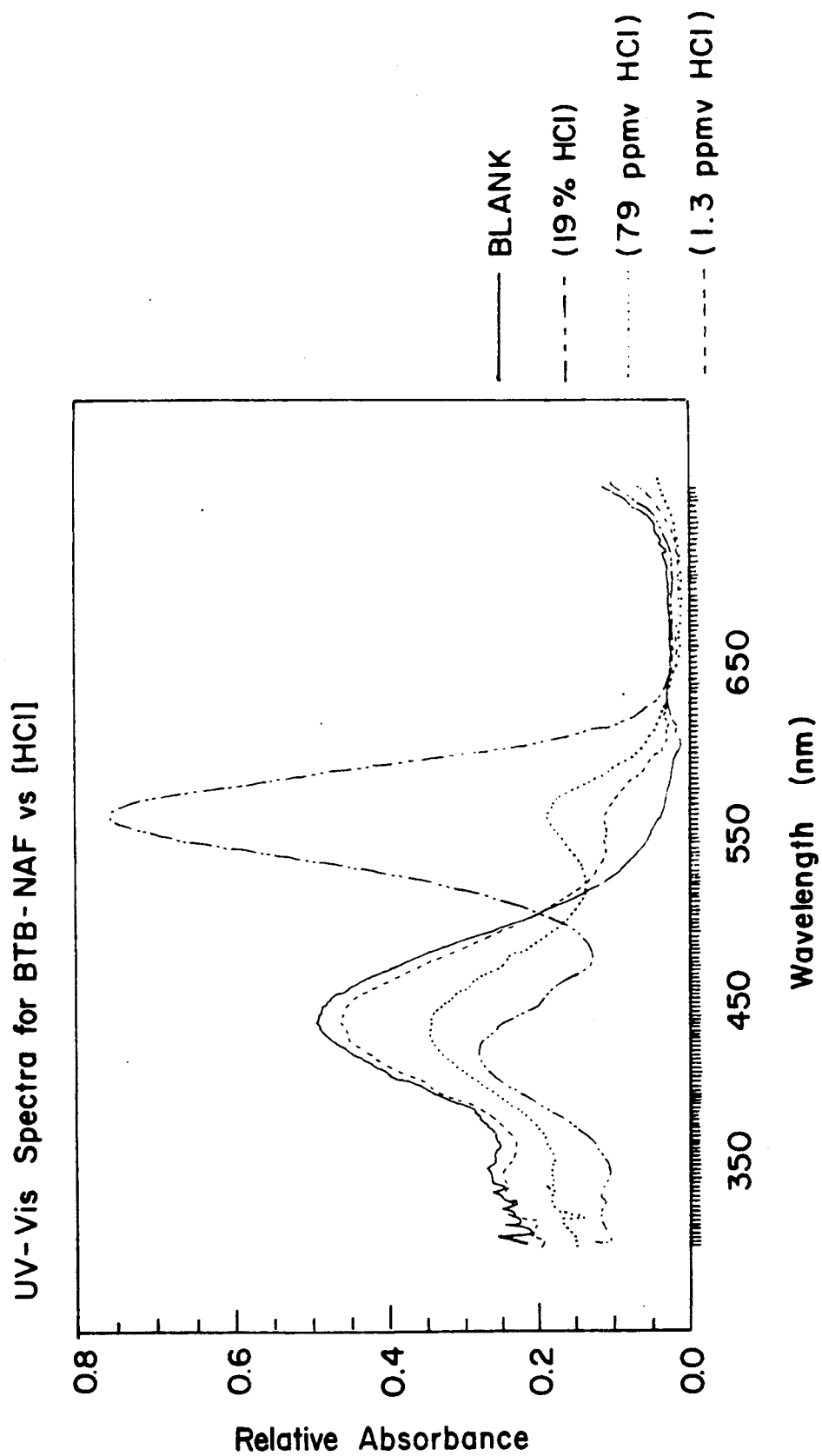

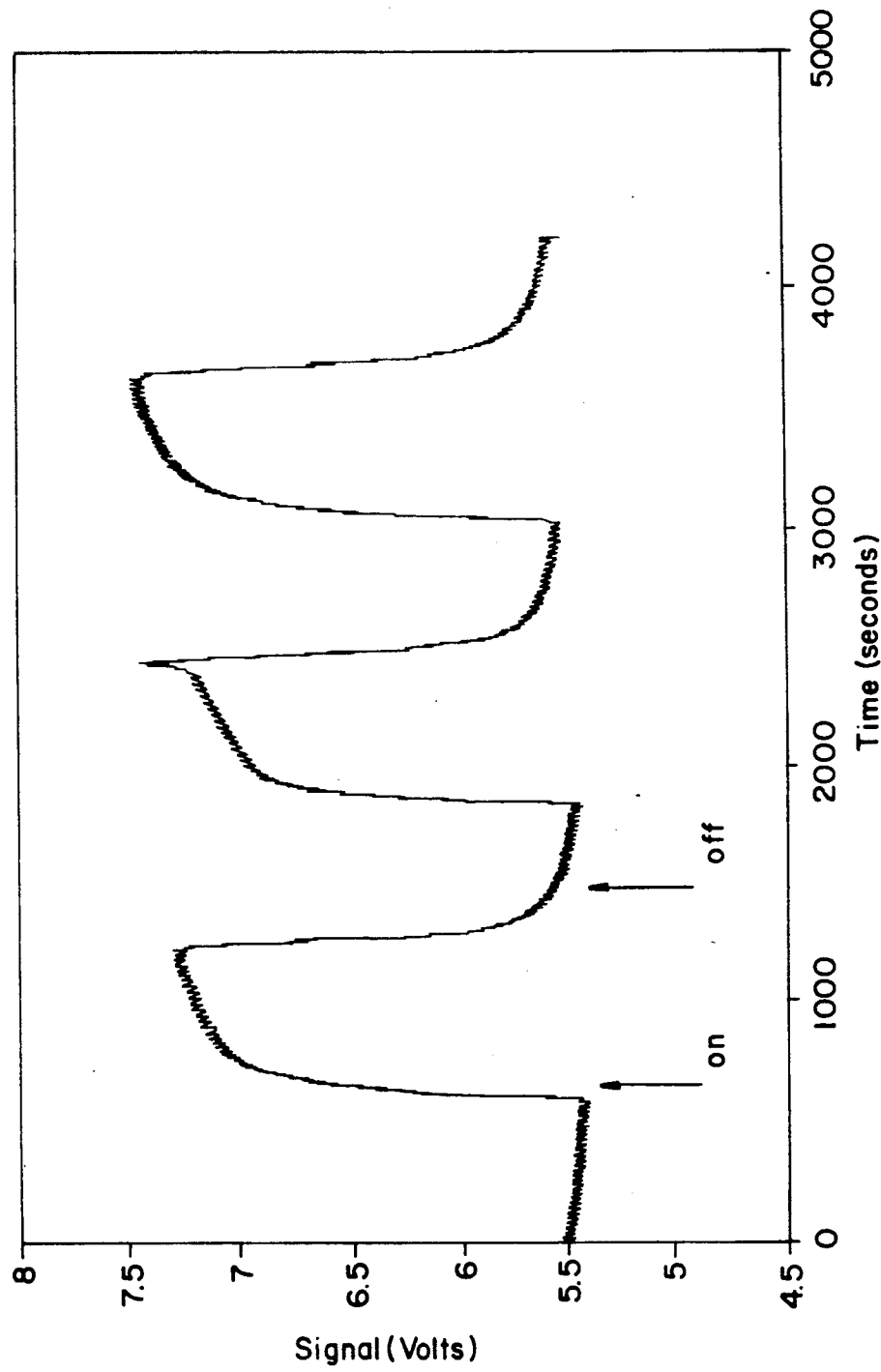

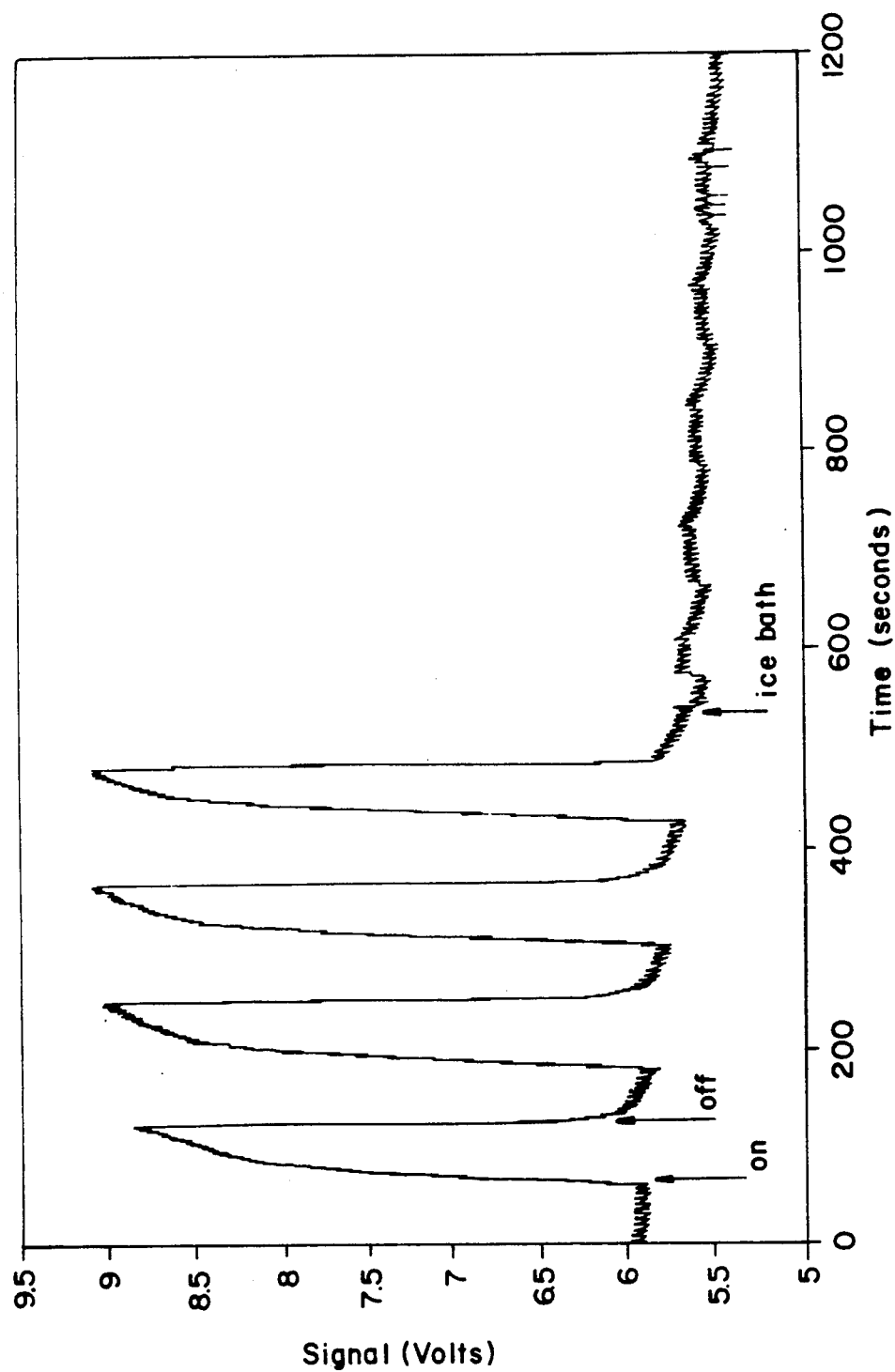

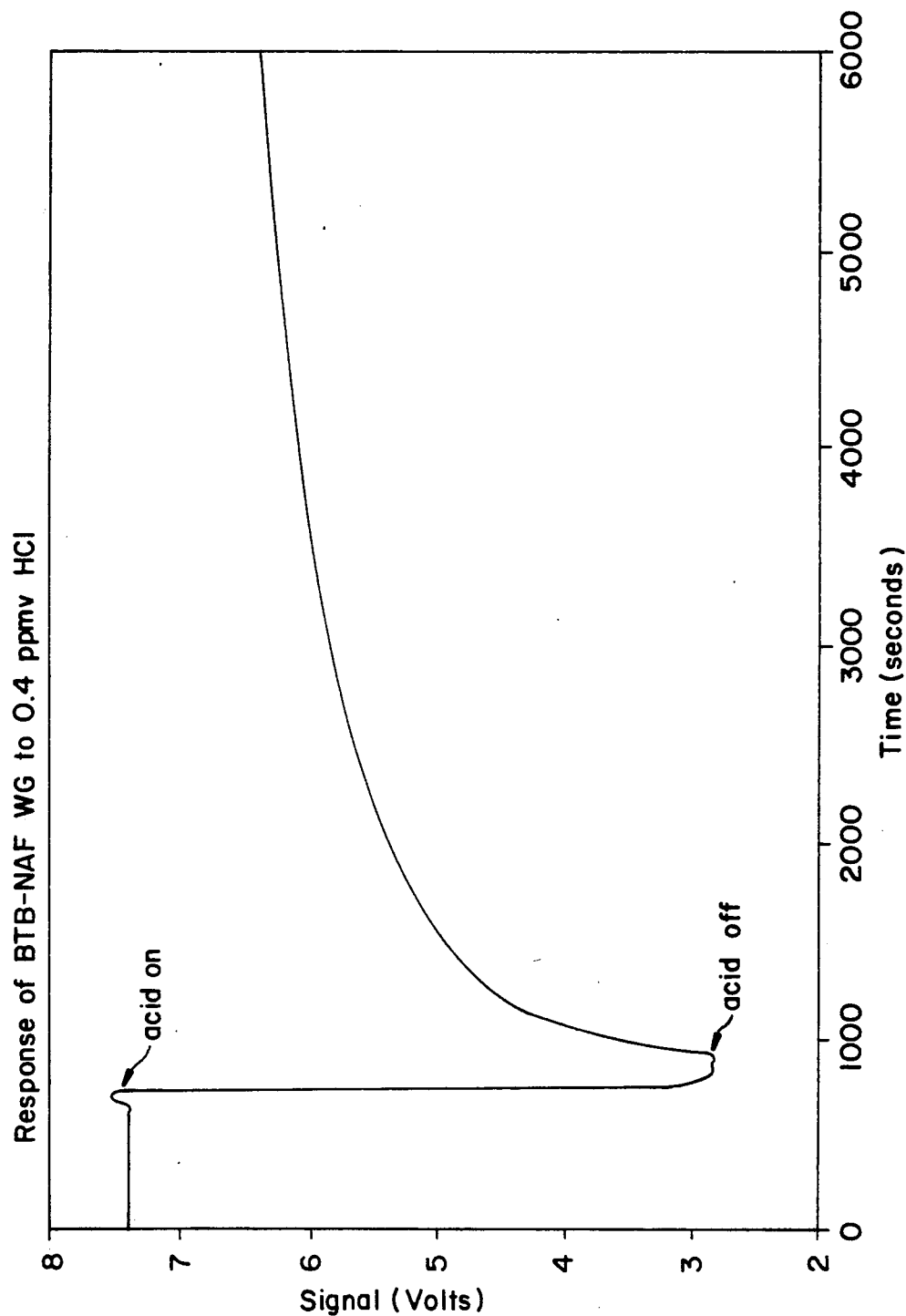

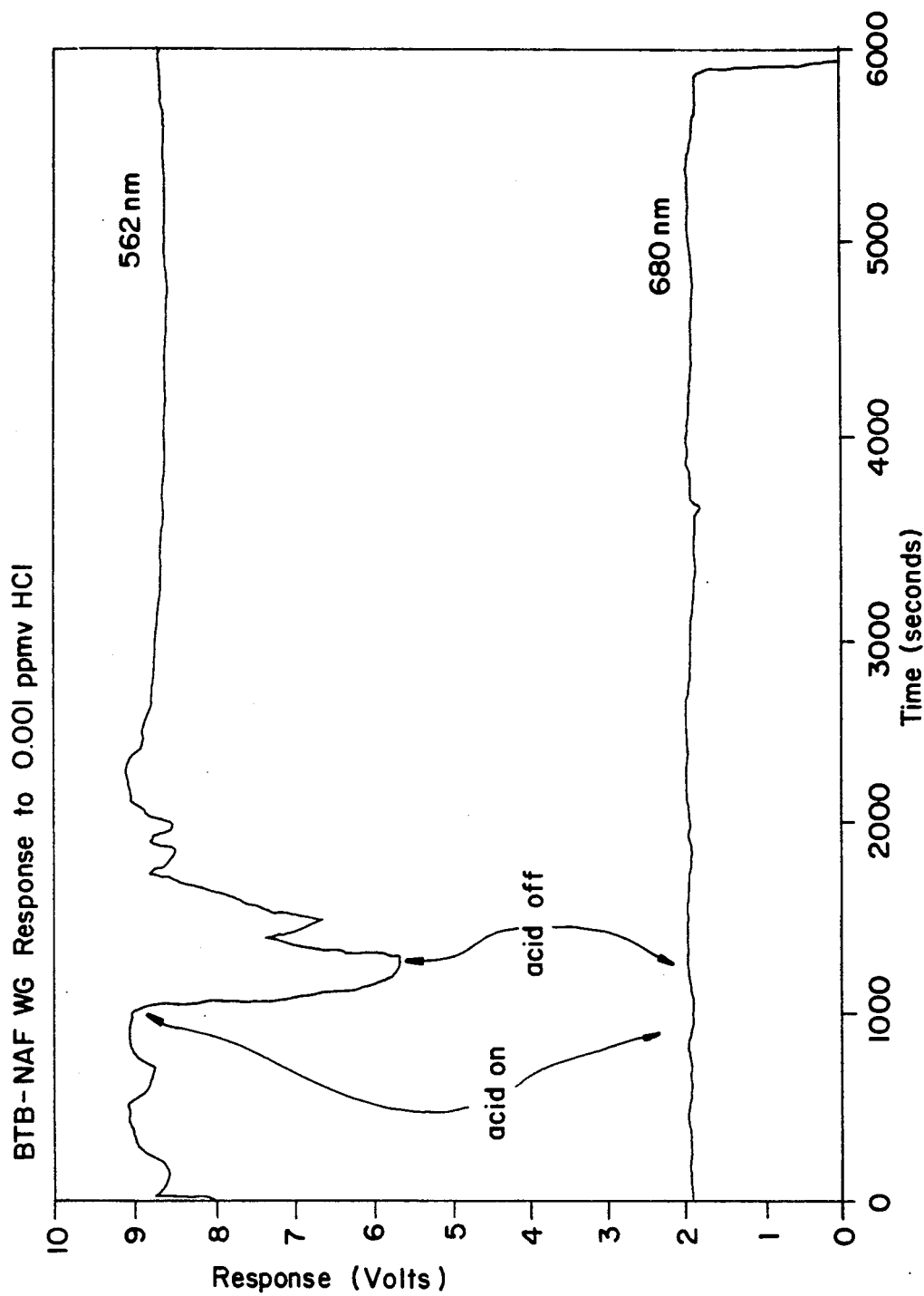

OPTICAL WAVEGUIDE VAPOR SENSOR

CONTRACTURAL ORIGIN OF THE INVENTION

The U.S. Government retains certain rights in this invention pursuant to an agreement between Transducer Research, Inc., and the Center for Disease Control/National Institute of Occupational Safety and Health under Grant No. 5 R44 OH02312-03.

BACKGROUND OF THE INVENTION

This invention relates to an optical sensor for the detection of gaseous air contaminants, especially acid vapors.

Chemical sensor technologies have been used increasingly for the detection or monitoring of hazardous vapors in the workplace environment. Applications include portable sensors or dosimeters to monitor individual personal exposure, or fixed-site sensors to monitor ambient concentrations of chemical species. The great attraction of these technologies is their capability for rapid, sensitive response at low cost.

It is an object of this invention to provide improved, portable, inexpensive, and selective chemical sensors for use in: protective equipment, such as gas masks, as an end-of-service alarm; dosimeters for monitoring individual exposure; or ambient air monitors.

It is a particular object of this invention to provide reliable sensors for the detection of acid vapors, such as vapors of HCl or $H_2S$.

It is another object of this invention to provide chemical sensors that use an optical waveguide which renders them substantially unsusceptible to electromagnetic interference.

It is yet another object of this invention to provide reliable sensors for the detection of basic vapors, such as vapors of ammonia, amines or hydrazines.

SUMMARY OF THE INVENTION

Briefly, the invention consists of an optical waveguide comprising a material whose light absorptivity changes upon exposure to a chemical vapor of interest. The waveguide may consist of a thin film of said material coating a thin, optically transparent substrate or else disposed on a tubular or rod-shaped optically opaque substrate so that multiple internal light reflections at the interfaces between the film and the substrate and between the film and air increase the optical path length through the film and thereby enhance the effects of any light-absorptivity changes within the thin film. Therefore, if the thin film comprises a substance whose absorptivity or other measurable light-interactive property at selected light wavelengths changes upon exposure to a vapor of interest, then measurements of the light transmission through the waveguide at such selected wavelengths will yield a sensitive indication of the concentration of that vapor in the ambient air.

In particular, for the detection of acid vapors, a preferred film composition comprises a reagent of bromothymol blue or thymol blue suspended in a polytetrafluoroethylene sulfonic acid (Nafion). The selected wavelength range is then 562.5±25 nm. A sensor using such a waveguide and light wavelength range exhibits generally sensitive and reversible responses to the protonic acid vapors, HCl and $H_2S$, but does not exhibit a measurable indicator response to the rather innocuous and omnipresent $CO_2$. The detection limit for $H_2S$ is estimated at <15 ppmv (parts per million by volume) and that for HCl vapor at <0.01 ppmv. The sensor is clearly several orders of magnitude more sensitive toward HCl than toward $H_2S$. This variable sensitivity for acid vapors appears to be due to the relative strength of the acid.

BRIEF DESCRIPTION OF THE DRAWINGS

The invention is best explained with reference to the drawings, in which:

FIG. 4 shows the UV-Vis (ultraviolet and visible wavelengths) spectra of a bromothymol blue indicator in a Nafion film exposed to dry air containing 1) 0% HCl 2) 19% HCl 3) 79 ppmv HCl and 4) 1.3 ppmv HCl;

FIGS. 5A–5B shows the response to water vapor of two different waveguide sensors;

FIG. 6 shows the response of one representative sensor to 0.4 ppmv of HCl;

FIG. 7 shows the response of the same sensor to 0.001 ppmv HCl using a 560-nm LED (top trace) and a 680-nm LED (bottom trace);

DESCRIPTION OF THE PREFERRED EMBODIMENT

Figure 1:
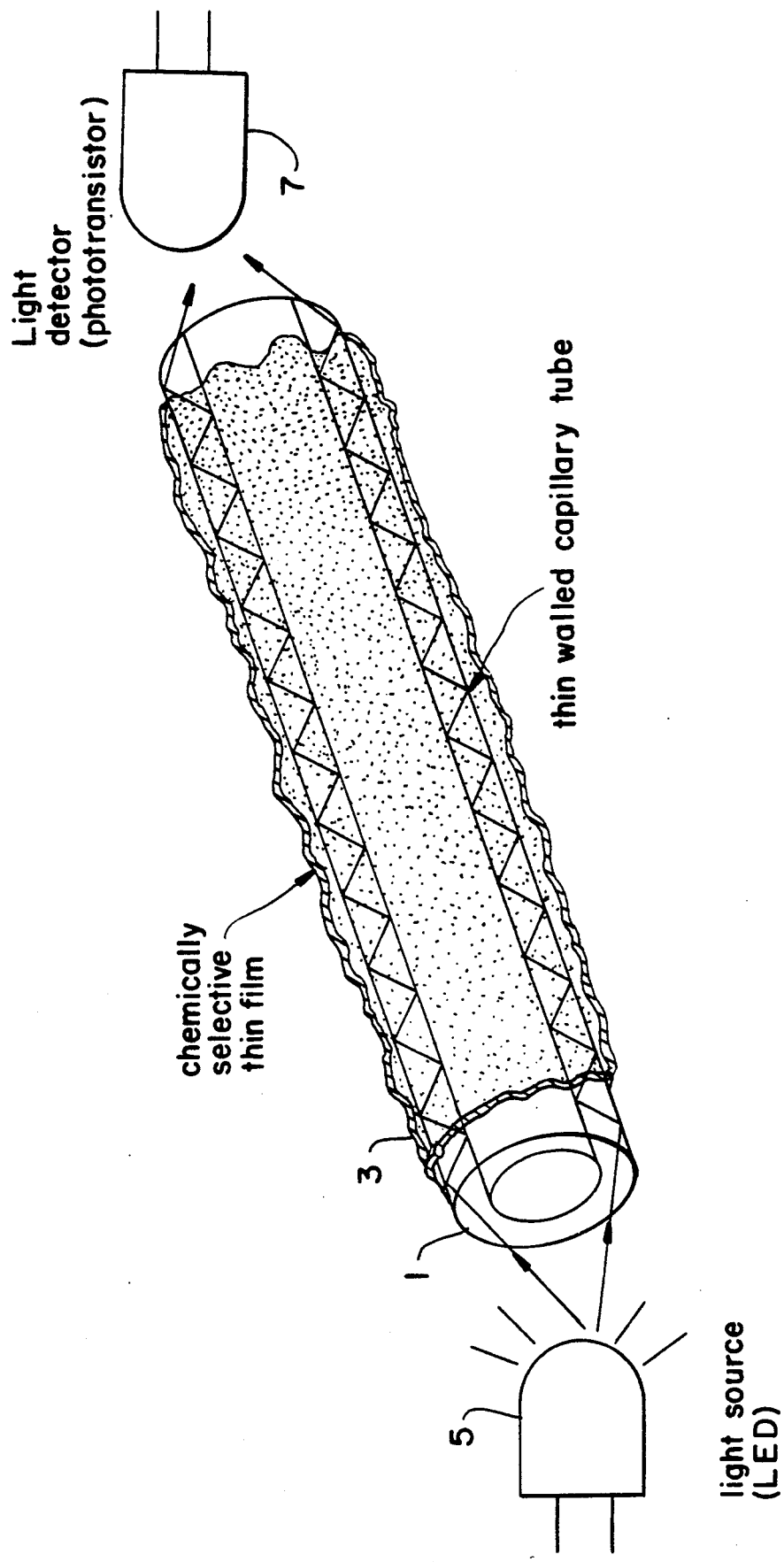
FIG. 1 is a schematic of an optical waveguide sensor utilizing multiple internal reflections.

A typical configuration of a waveguide sensor with multiple internal light reflections (MILR) is illustrated in FIG. 1. The waveguide consists of a thin, optically transparent substrate 1 coated with a chemically sensitive reagent film 3. A light source 5 focused on one end of the waveguide introduces radiant energy of an appropriate wavelength (and bandwidth) to the waveguide. This radiant energy then propagates by MILR along the length of the waveguide. At the opposing end of the waveguide, the exiting light is focused onto an optical detector 7. The evanescent wave associated with the propagating light wave can probe the region near the surface of the substrate as it is reflected at the interface. This evanescent wave can interact with thin films in contact with the substrate surface. Any change in the optical properties of the reagent film that result in a change in the intensity of light reaching the detector constitutes a sensor response. These changes, arising from various possible electromagnetic interactions with matter, can be observed by measuring such properties as absorbance, scattering, fluorescence or luminescence. If these changes occur in response to chemical stimuli, then the waveguide acts as a chemical sensor.

Figure 2:
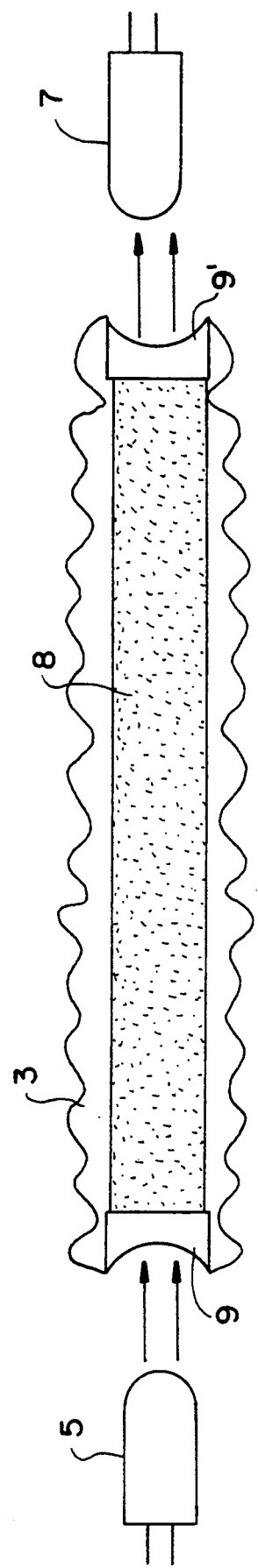
FIG. 2 is a schematic of an alternative optical wave guide sensor.

In an alternative embodiment shown schematically in FIG. 2, the chemically sensitive film 3 is covering a rod-shaped substrate that is opaque to the wavelengths of interest throughout most of its body 8 onto whose ends are cemented optically transparent lens-shaped discs 9 and 9' of the same diameter as the body 8. Light form a light-emitting diode (LED) 5 is focused onto disc 9 and transmitted therefrom to the coating 3 and thence to the second end disc 9' from which it is directed onto a phototransistor (PT) 7. In this embodiment, film 3 alone acts as the waveguide.

The ideal sensor characteristics include the following: rapid, sensitive response; reproducibility; selectivity; small size and portability; low cost; and low power consumption. For optical sensing systems, the critical components include the colorimetric reagents(s), the radiative source, the waveguide and its geometry, and the detector. Each of these system components is considered with respect to its impact on the desirable sensor characteristics listed above.

Light Sources and Detectors

The ideal light source must exhibit stable output of sufficient intensity in the spectral region of interest. While many sources possess these qualities, they are of limited utility for sensor applications. Tungsten lamps or lasers, for example, may be suitable for remote sensing using fiber optic probes. They are unsuitable, however, for the portable sensor of the present invention. These sources have high power requirements and are relatively expensive. Similar arguments can be made regarding most optical detectors, such as photomultiplier tubes. Miniature electronic components are available, however, that can serve as sources and detectors for a waveguide sensor. The advantages of these components are their small size, low cost, and low power requirements.

The ideal sources are LEDs. These are readily available at low cost from commercial sources, having maximum emission output in the spectral region between 550–680 nm. Typical bandwidths for these sources are on the order of 10–50 nm. These sources are not as intense as other sources, and thus are not well suited as excitation sources for fluorescence techniques. They are of sufficient intensity, however, to achieve the required response sensitivity and detectability for absorbance-type sensors. As detectors, inexpensive PTs are available that respond to light in the visible region.

Colorimetric Reagents

Colorimetric detectors for a wide variety of chemical air contaminants have been developed, as listed, for instance, in "Detector Tube Handbook," K. Leichnitz (compiler) and A. Foster (translator), 5th Edition, Dragerwerk AG, Luebeck, Feb. 1983. The preferred acid-sensitive colorimetric reagents are the pH indicators. These materials exhibit changes in their absorbance or fluorescence properties in the visible region upon exposure to acid vapors. Thus, these materials were evaluated for use with the waveguide sensor. The following criteria were used in the selection process:

1. The reagent must be stable in air.
2. It must form thin films with good adhesive properties when suspended in polymer films.
3. The spectral properties of the reagent indicator must be compatible with the sensor source and detector components under consideration; i.e., the resulting film must exhibit a change in a selected wavelength region upon exposure to acid vapor.

For the sensor configuration of FIGS. 1 and 2, the fluorescence indicators would not be suitable for several reasons. First, the sensitivity of fluorescence techniques is dependent on the intensity of the source, and LEDs are not very intense light emitters. Second, the PT detector has a level response over a broad spectral region and could not distinguish between source radiation and indicator fluorescence without appropriate in-line filters. Thus, absorbance-type indicators are preferred for these sensors.

Preferred Materials and Components

A variety of polymers and pH indicators were tested as potential sensor films. These materials and relevant data are listed in Table 1a. Among the tested polymers were polyisobutylene (PIB), polyvinyl alcohol (PVA), polyvinylpyrrolidone (PVP), polyethylene glycol (PEG), polyethyleneimine (PEI), and a perfluorinated sulfonic acid polymer, Nafion (NAF; 5% solution in alcohol). The Nafion was obtained from Solution Technologies (Mendenhall, Pa.); the remaining polymer materials were obtained from Aldrich (Milwaukee, Wis.). All materials were used as received. With the exception of PIB, these polymers contain proton donor and/or proton acceptor functionalities. One of these polymers (Nafion) is an ionomer containing sulfonic acid groups attached to a perfluorinated polyethylene backbone. Nafion is of particular interest because it can be processed into thin membranes that are well suited for an optical sensor. These materials were evaluated on the quality of the resulting films when cast on a glass surface.

TABLE I

Indicator and Polymer Properties

A. Coating Materials - Polymers and Indicators

| Polymers | MW Range | Indicators | pH Transition Range |
|---|---|---|---|
| PIB | 380,000 | Thymol Blue | 1.2–2.8; 8.0–9.6 |
| PVA | 31–50,000 | Bromothymol Blue | 6.0–7.6 |
| PVP | 40,000 | Bromcresol Green | 3.8–5.4 |
| PEG | 600/1500 | Litmus | 5.0–8.0 |
| PEI | 50–60,000 | Methyl Red | 4.8–6.0 |
| Nafion | (unknown) | Bromcresol Purple | 5.2–6.8 |
|  |  | Phenolphthalein | 8.0–9.6 |

B. Indicator/Polymer Film Behavior:

| Coating | Dry color | Acid Exposure[1] | Base Exposure[1] |
|---|---|---|---|
| BTB/NAF[2] | violet | yellow → violet (R) | yellow → blue (R) |
| BCG/PVP | blue/green | blue → yellow (N) | yellow → blue (R) |
| MR/PEG | red orange | orange → purple (R) | orange → yellow (R) |
| BCG/PEG | yellow | yellow → colorless (R) | yellow → blue (R) |

[1]The acid and base responses were reversible (R) or non-reversible (N), as indicated.
[2]The BTB/NAF film dries in the acid (violet) form, but can be converted to the neutral (yellow) form by exposure to water vapor.

Indicators were selected on the basis of the observed color transitions and of the pH transition ranges. Available indicators included thymol blue, bromothymol blue, litmus, phenolphthalein, methyl red, bromcresol purple, and bromcresol green (see Table I). The majority of these indicators undergo a visible color change when exposed to slightly acidic conditions. The notable exceptions are phenolphthalein (transition in the basic range) and thymol blue (transition in the low pH/strong acid range).

Optical electronic components (LEDs, PTs) for the construction of the sensor were obtained from Newark Electronics (Chicago, Ill.).

Electronic Circuitry

Figure 3:
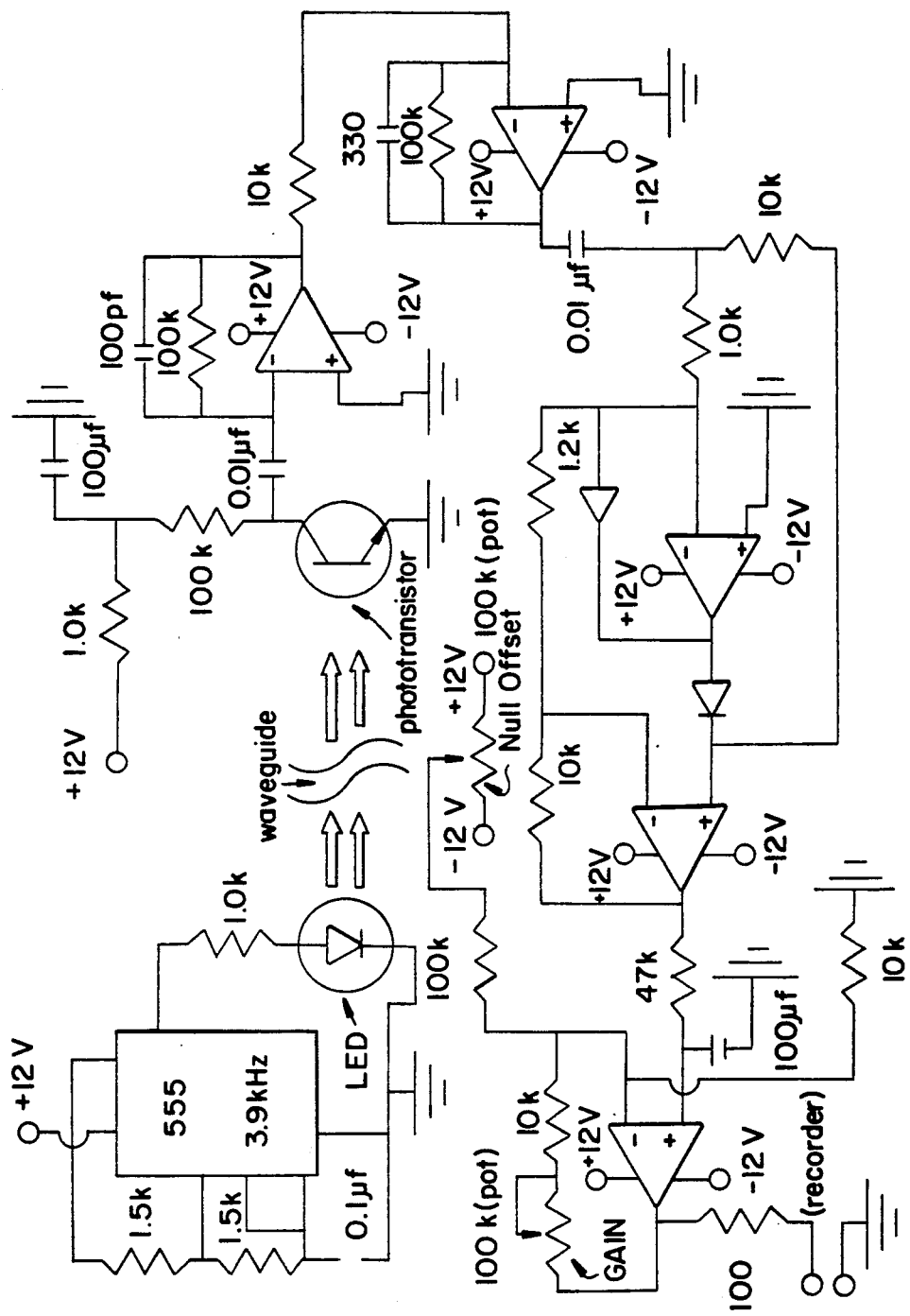
FIG. 3 is a circuit diagram for the sensor electronics.

Signal detection is achieved using the electronics module constructed according to the schematic diagram of FIG. 3. The module consists of two separate circuits. The first circuit drives the light source (LED), while the second circuit amplifies and filters the signal from the detector (PT) prior to its output to the data recording system. The LED source is pulsed at 3.9 kHz using an eight-pin integrated-circuit (IC) timer chip (Catalog No. LM555, National Semiconductor Corp., Santa Clara, Calif.). Pulsing of the light source is necessary to minimize temperature drift in the photodetector signal. In addition, use of an oscillating source permits filtering of the resulting signal to improve the signal-to-noise ratio. The detection and amplification circuit consists of several amplification stages and a rectifier stage, using eight-pin IC amplifier chips (LM741, National Semiconductor Corp., Santa Clara, Calif.). The amplification stages contain high-pass filters to remove 60-cycle interference and RC (resistance- capacitance) filters to minimize the effects of voltage spikes in the final signal. Amplification of the signal can be controlled using a 10-turn 100-kilohm variable resistor (GAIN), and the zero level can be adjusted using a NULL OFFSET potentiometer. The 0% and 100% transmittance signals are adjusted to be compatible with the data-acquisition computer. Data processing for the spectral and waveguide measurements can be performed with a microprocessor (not shown).

Coating Selection

Solutions were prepared by dissolving the polymers and indicators in suitable solvents, usually pure or aqueous methanol. Final solutions contained approximately 1 mg/mL of polymer and indicator. Test films were prepared by casting a small volume of the solution(s) on the surface of clean glass slides and allowing the solvent to evaporate. The resulting films were then evaluated based on film quality and response characteristics, as described below. These films were then exposed to HCl vapor to determine relative response behavior. The results of these preliminary screening tests are summarized in Table 1b. Several of the indicators (phenolphthalein, litmus) failed to exhibit an acceptable color change upon exposure to the acid. Other indicators gave a good visible color-change response to acid vapor in some polymers but not in others. PIB-indicator films gave no response, which supports the observation that the polymer must exhibit some proton donor-acceptor behavior in order to activate the proton-transfer indicator color change. Some acid response was exhibited by the PEG-indicator films, but the PEG produced viscous, oily films that were difficult to work with in this sensor application. PVA films showed poor reversibility upon exposure to and removal of acid vapors. The most promising results were obtained using the bromcresol green/polyvinylpyrrolidone (BCG-PVP) and bromothymol blue/Nafion (BTB-NAF) films. Both of these indicator films had good adhesion properties and dried to produce robust thin films exhibiting uniform surface coverage. The BCG-PVP film exhibited a blue color upon drying, typical of the basic form of the indicator. Exposure to acid resulted in an irreversible conversion to the acid form (yellow) which persisted after removal from the acid vapor. Subsequent exposure to NH3 vapors produced a blue color, which reverted to the yellow form upon exposure to dry air. This indicator film should be suitable as a dosimeter for acid gases or for on/off alarm applications. In its acid-treated form, the BCG-PVP film can be used as a reversible sensor for basic vapors, especially vapors of NH3.

The BTB-NAF film dried in the acid form (violet), but exposure to water resulted in conversion to the neutral form (yellow orange). This film exhibited reversible response to HCl vapor. Initial exposure to acid produced the violet color, which recovered slowly to the neutral form after removal from the acid. Because of the reversible nature of this indicator film to acids, it was selected as the preferred embodiment for an acid vapor sensor.

Absorption Spectra

The BTB-NAF coating was evaluated by UV-Vis spectroscopy to determine appropriate wavelengths to be used for the selection of components in the construction of an optical waveguide sensor. A thin film was coated on a quartz slide that was placed inside a flow cell. Spectral scans were performed while acid vapors of varying concentrations were passed through the cell. Acid vapors were generated by bubbling a dry air carrier through a flask containing HCl solutions of varying concentrations.

FIG. 4 shows the spectra for the film under exposure to HCl vapors from solutions of different concentration. The BTB-NAF film exhibits two absorbance maxima, each of which exhibits dependence on acid vapor concentration. The first maximum occurs at 435-nm and corresponds to the yellow form of the neutral indicator. As the film is exposed to increasing concentrations of acid vapor, the 435-nm peak decreases and undergoes an apparent slight blue shift, while there is a corresponding increase in absorbance at 562 nm. The 562-nm peak corresponds to the violet (acid) form of the indicator.

Sensor Responses

Sensor response is determined by an increase in absorption (i.e., decrease in light intensity as measured by the detector at 562 nm for the acid form of the indicator. The long-term and short-term waveguide responses to acid vapors are not straightforward, and appear to be dependent on three separate phenomena. These phenomena include water sorption by the Nafion, irreversible interactions between the acid vapor and the Nafion, and the interaction between the indicator and the acid vapor. These factors are discussed in more detail below.

The sensor response to water vapor is summarized graphically in FIG. 5. In FIG. 5a (insert) the response of a Nafion film to water vapor is presented. The introduction of only water vapor to the Nafion coated waveguide results in an increase in transmittance of nearly 40%, or 2 volts. This increase in transmittance is reproducible upon repeated exposure to water vapor. FIG. 5b shows the response of a waveguide (WG) coated with a bromothymol blue-Nafion film. The first four exposures represent responses to nearly saturated water vapor, produced from a bubbler at room temperature. Five subsequent exposures were made using a bubbler that was maintained in an ice bath, and produced only a slight increase in transmittance. This increase in response to water vapor constitutes a potential interference.

EXAMPLE 1

Using the spectral data of FIG. 4, a yellow LED having maximum emission intensity at 562.5 nm was selected as the source. This wavelength corresponds to the absorbance maximum for the film in the acid (violet) form. Thus, an increase in acid concentration should result in an increase in absorbance at this wavelength and produce a corresponding decrease in the intensity of the light reaching the detector. A sensor based on the configuration of FIG. 1 was constructed. The detector consisted of a PT. The WG consisted of a thin-walled glass capillary tube (75 mm long, 1.2 mm O.D., 0.2 mm wall thickness) coated with the film. Thin-walled substrates are desirable to maximize the number of internal reflections, and thereby increase the interaction between the propagating light wave and the reagent film. A small-diameter plug (not shown) was inserted inside the capillary to block light travelling down the center of the tube. Thus, only light that has traversed the waveguide via reflections inside the capillary walls reached the photodetector. The LED-WG-PT components were held in rigid contact using plastic rods that have been drilled out to accommodate the optical components and the WG. The entire sensor configuration was enclosed by a glass tube (not shown) having inlet and outlet ports to introduce and vent the carrier and acid vapor streams.

For this sensor, any change in the optical properties of the film that translated into a change in light intensity reaching the photodetector affected the analytical signal. A typical response of the BTB-NAF optical waveguide sensor to 0.4 ppmv HCl is given in FIG. 6. Upon exposure to the acid vapor, the signal from the PT decreased rapidly, in consistency with the increase in absorbance at 562 nm by the acid form of the indicator. Removal of the acid vapor resulted in a slow return to the neutral form. A more rapid recovery could be accomplished by exposing the sensor to base and/or water vapor; in any event, the signal failed to return completely to the original baseline response. Repeated exposure to high acid concentrations resulted in a gradual decrease in light transmission. It is worth noting that repeated exposure of the sensors to acid vapor produced a very reproducible minimum signal, even though the sensor signal did not return to the original signal after removal of the acid vapor.

To verify that the observed response was, in fact, the result of absorbance by the indicator, the following experiment was performed. The sensor was exposed to 0.001 ppmv HCl while the transmittance was monitored upon illumination of the WG with a yellow-green (562-nm) LED. This experiment was repeated using a red LED source, having a maximum emission intensity at 680 nm. This wavelength is well removed from the maximum absorbance wavelengths for the acid form (562 nm) and neutral form (435 nm) of the indicator. The results are presented in FIG. 7. At the 680-nm wavelength, the change in signal upon exposure to acid (bottom tract) is insignificant, whereas the sensor exhibits a significant decrease in signal at 560 nm, confirming that the observed signal is due to absorbance by the acid form of the indicator.

EXAMPLE 2

Figure 8:
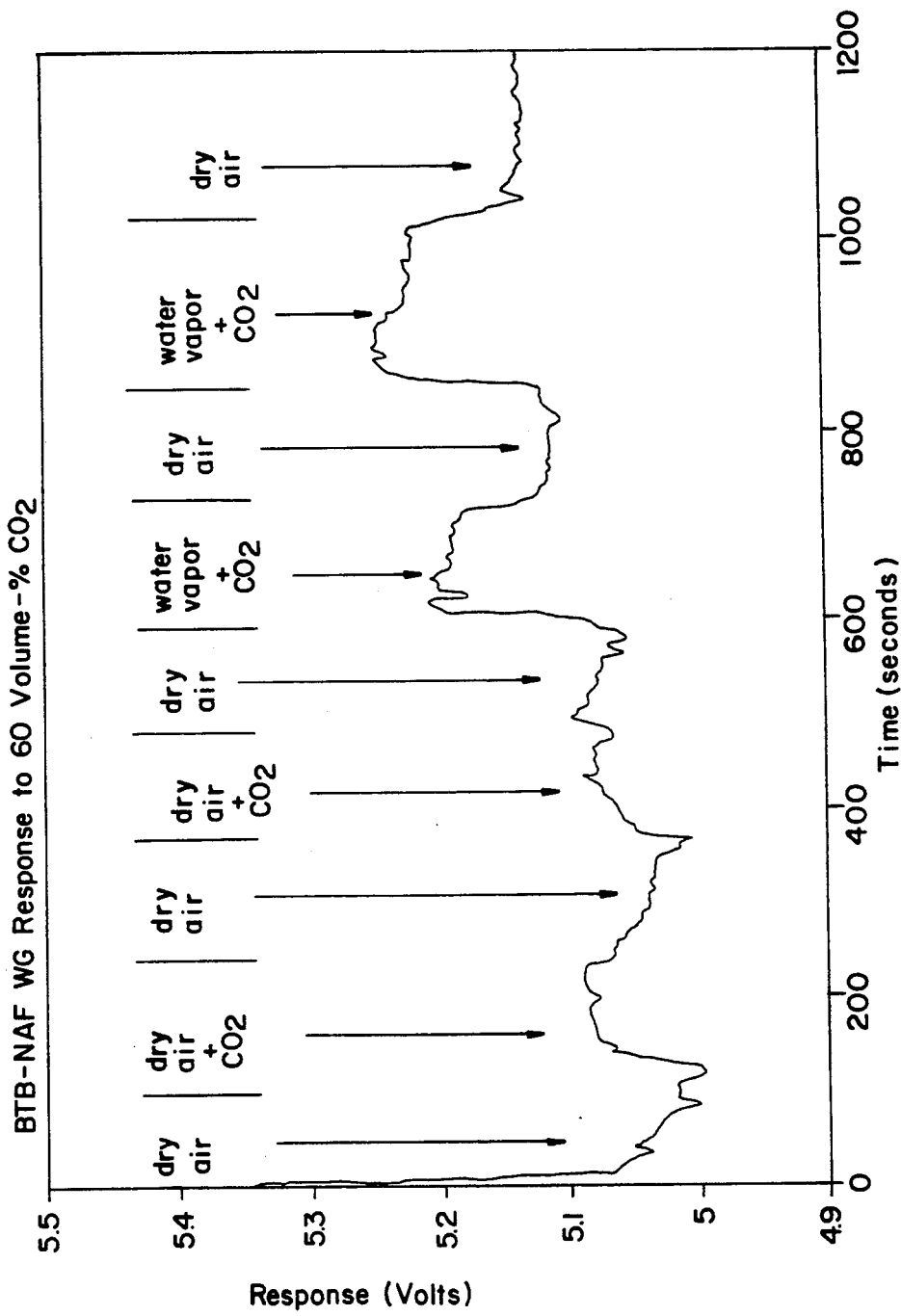
FIG. 8 shows the sensor responses to 60 volume-% $CO_2$ in dry and in humidified nitrogen.

One of the proposed uses of the sensor of Example 1 is as a monitor in protective equipment, such as a gas mask. In such an environment, the sensor could also be exposed to exhaled gases, including $CO_2$ and water vapor. This combination of gases could potentially form an acidic mixture. The sensor response to combinations of these gases is displayed in FIG. 8.

Vapor streams of dry nitrogen, dry nitrogen+$CO_2$, and water vapor+$CO_2$ were sent to the sensor. In each case, the $CO_2$ concentration was 60% by volume. Upon exposure to dry air+$CO_2$, there is a slight increase in the sensor signal, and a return to the original baseline when the $CO_2$ is removed. When water vapor is included in the $CO_2$ stream there is an additional small increase in signal. This is consistent with the WG response to water vapor as noted above. The total response to $CO_2$(g) under the test conditions was an increased signal of $\approx$100-150 mV. To counteract this increase in signal would require an indicator response (signal decrease) equivalent to $3 \times 10^4$ ppmv HCl. From these results, it is concluded that $CO_2$ alone does not constitute a significant interference. The $CO_2$ with water could produce a protonic acid that would be expected to produce an indicator response, since the indicator undergoes a transition as a result of a proton transfer reaction. The fact that no response is observed, even in the presence of water, may be due to the fact that carbonic acid ($H_2CO_3$) is a very weak acid. The free proton concentration from carbonic acid is about seven orders of magnitude less than from a comparable concentration of HCl.

EXAMPLE 3

Figure 9:
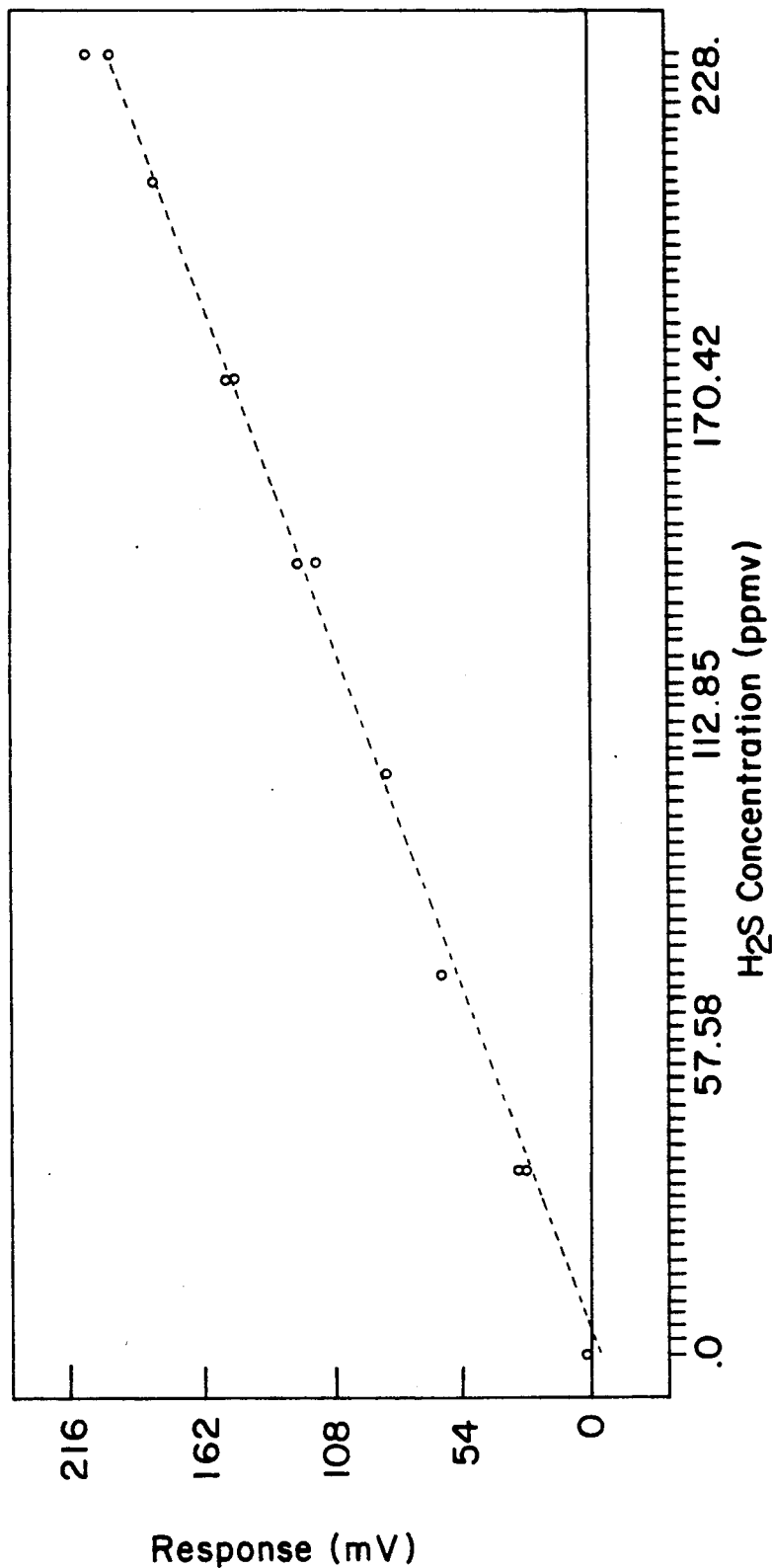
FIG. 9 is a calibration curve for the same sensor, demonstrating a linear response to $H_2S$ between 0 and 228 ppmv.

The output (in mV) of the sensor of Examples 1 and 2 was monitored with a strip chart recorder as the sensor was exposed to alternating streams of dry air and $H_2S$-$N_2$ mixtures of varying concentrations at flow rates of approximately 200 mL/min. The $H_2S$-$N_2$ gas mixture was diluted with laboratory air that was scrubbed with a charcoal-molecular sieve trap. Thus, the final mixture contained some $O_2$ but a minimal concentration of water vapor. The results are summarized in FIG. 9. The sensor exhibits good linearity of response to $H_2S$ over the concentration range studied (0–228 ppmv). Assuming a signal-to-noise ratio of three as the detection limit, and using a value of 5 mV for the root-mean-square sensor noise, a minimum detectability of 15 ppm $H_2S$ is calculated.

EXAMPLE 4

Repeated exposure of films resulted in a gradual decrease in sensor response in the form of a long term reduction in the sensor baseline signal. It was postulated that the Nafion was undergoing fatigue upon acid exposure, resulting in an irreversible decrease in transmittance properties.

Figure 10:
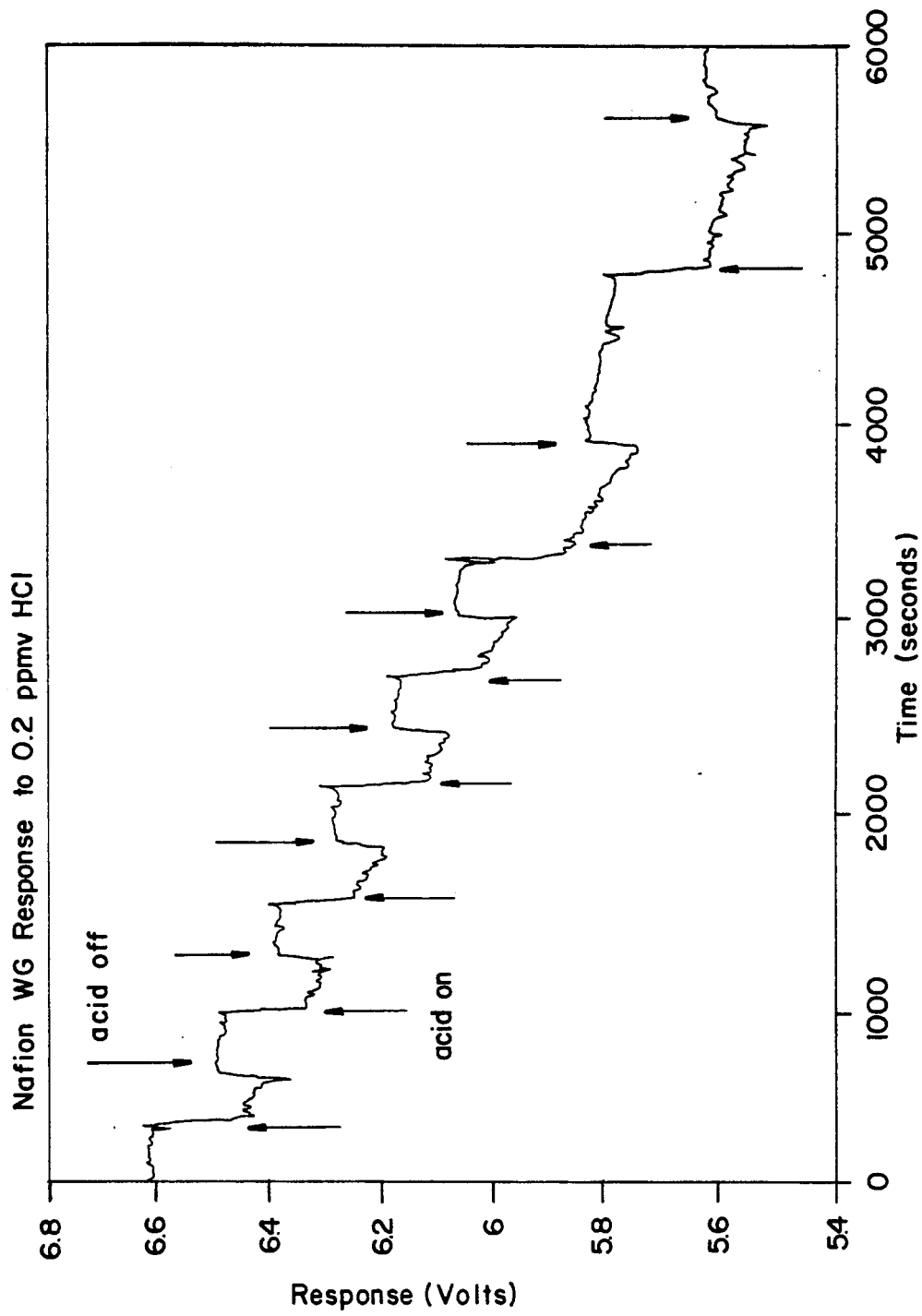
FIG. 10 shows the changes in transmittance of a Nafion-coated waveguide upon repeated exposures to 0.2 ppmv HCl.

Waveguides coated with Nafion films (without indicator) were exposed to acid vapors, and the transmittance at 562 nm was monitored. The results are presented in FIG. 10. The test was performed using 0.2 ppmv HCl. As the Nafion film was exposed to repeated one-minute cycles of dry air and acid vapor, the sensor baseline steadily decreased. Upon exposure to acid vapor, the sensor response undergoes a reproducible decrease of approximately 170 mV. Returning to dry air results in a partial recovery of the sensor signal, but there is still a net irreversible signal change of approximately 110 mV. The extent of irreversible signal decrease seems to increase as the acid concentration increases, and constitutes a dosimetric response. The 170-mV response of the Nafion sensor to 0.2 ppmv HCl (FIG. 10) can be compared with the nearly 4.5 Volt response of the BTB-NAF film to 0.4 ppmv HCl (FIG. 6). Obviously, the indicator response is nearly 20 times more sensitive to acid vapor than the Nafion alone.

Sensor Configurations

As is evident from FIG. 5, the sensitivity of the WG can be compromised by the presence of water vapor. The polymer used as the supporting matrix for the indicator reagent interacts with water vapor to produce an increase in transmittance, which constitutes a systematic interference. The normal indicator-acid response produces a decrease in the transmittance of the sensor. Three dual-sensor configurations are presented in FIGS. 11, 12, and 13 that may correct for the water vapor interference.

Figure 11:
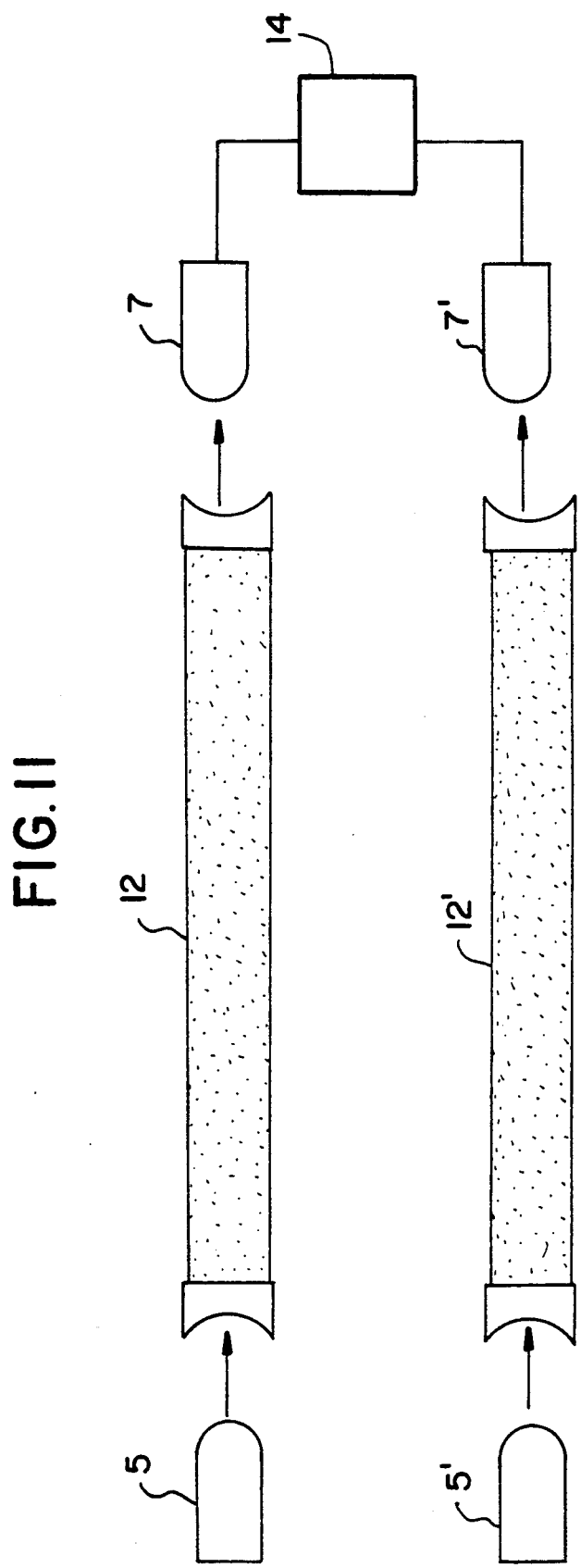
FIG. 11 is a block diagram of a dual sensor configuration using two different light wavelengths to compensate for the effects of water vapor.

In FIG. 11, two waveguides 12 and 12' are coated with identical BTB-NAF films, with each waveguide having its own photodetector 7 or 7' and LED 5 or 5'. One LED emits at 562 nm, while the other LED emits at 680 nm. The 562-nm sensor response is the net result of both water and acid vapors, whereas the 680-nm response is due only to water vapor. A microprocessor-controlled electronic circuit 14 takes the difference between the two responses and corrects for the effects of water on the acid sensor response.

Figure 12:
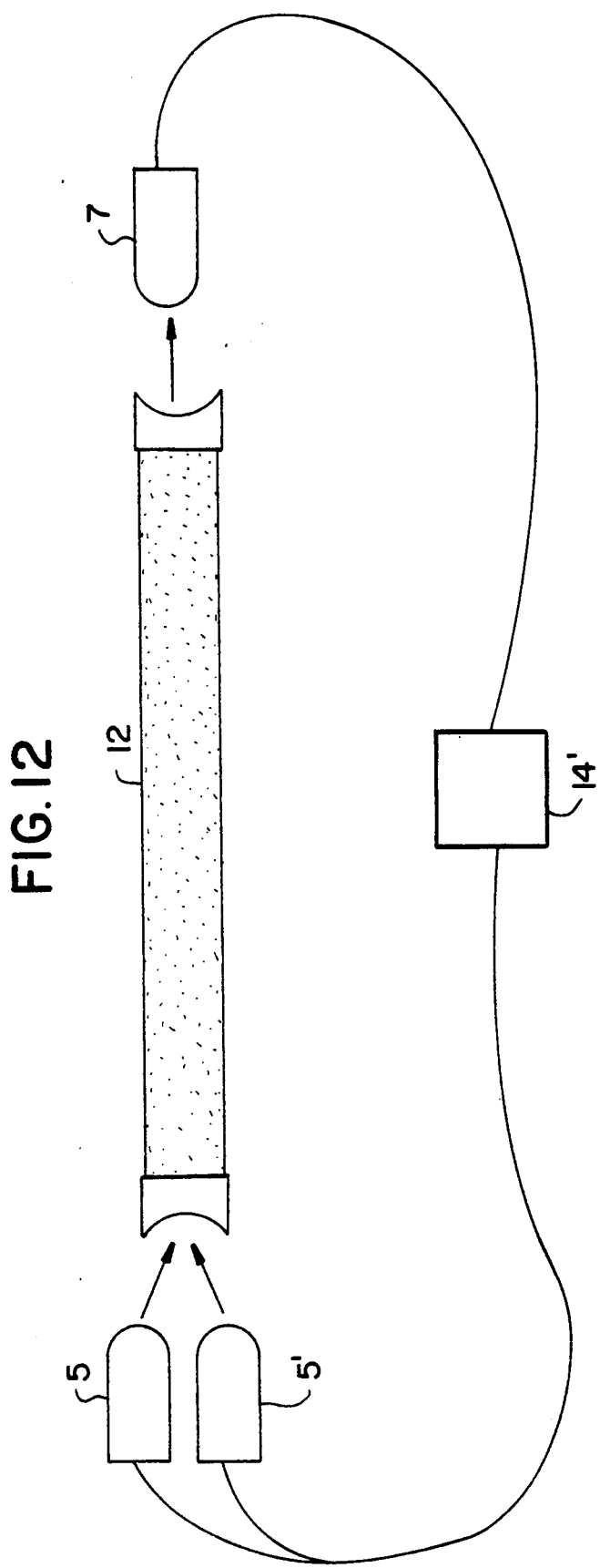
FIG. 12 is a block diagram of an alternative dual-wavelength configuration.

A simplified version of the approach of FIG. 11 is shown in FIG. 12, where the two different LEDs, 5 and 5', are focused onto the same waveguide 12 and the circuit 14' includes a timing circuit (not shown) that causes the two diodes to go on and off in brief alternate cycles.

Figure 13:
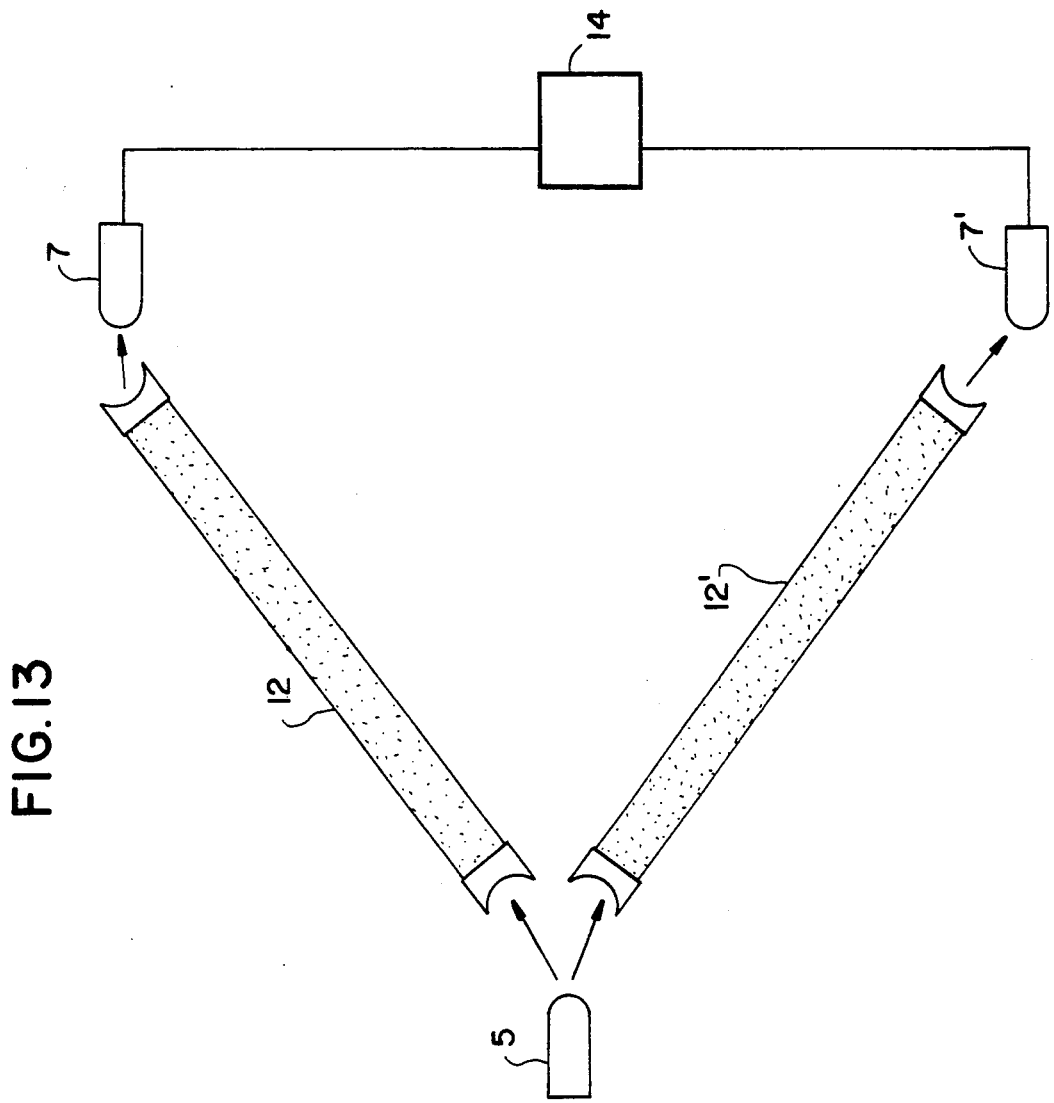
FIG. 13 is a block diagram of an alternative compensating dual-sensor configuration.

The configuration of FIG. 13 uses only one LED of 562 nm wavelength. The two waveguides 12 and 12' are coated with BTB-NAF and Nafion films, respectively, and each has its own photodetector 7 or 7'. The Nafion film responds to water only, while the BTB-NAF film responds to both water and acid. Again, circuit 14 yields the difference between the two signals corresponding to the acid response.

The effects of Nafion of long term acid exposure and of potential interferences from water and acid must be considered. While long term acid exposure will produce a decrease in transmittance, this effect is not serious. First, the magnitude of transmittance decrease is smaller than the indicator-acid response by a factor of 20 or more. Second, the time frame over which this effect would become a problem is long compared to the time frame in which the indicator response to acid would signal the end of service of an acid-scrubbing filter. Finally, both the acid effect on Nafion and the acid-indicator response produce a decrease in transmittance, so that the cumulative effect would be a long-term decrease in the transmittance in the presence of acid. This effect will be more dramatic at higher acid concentrations. If this sensor is used as an alarm device to signal the end of service for protective equipment (gas masks), then it will produce an alarm response before high acid concentrations are present. Thus, the useful lifetime of the sensor should not be affected by this phenomenon.

There will now be obvious to those skilled in the art many modifications and variations of the afore-disclosed embodiments which, however, will remain within the scope of the invention if defined by the following claims.

We claim:

1. A sensor for detecting a selected air constituent comprising: an optical waveguide having a front end and a rear end; a light source for transmitting light of a selected wavelength to one end of the waveguide; and means for measuring the intensity of light emitted from the other end of the waveguide, said waveguide comprising a film of material disposed on a substrate such that multiple internal light reflections occur at the interfaces between the film and the substrate and between the film and air, said material having optical properties that are susceptible to change in the presence of said air constituent, wherein said film comprises a reagent embedded in or forming a part of a polymer, said reagent yielding a substance having characteristic light-transmissive or light-adsorptive properties upon exposure to said air constituent.

2. The sensor of claim 1, wherein:
said light source is a light-emitting diode;
said photodetector is a phototransistor; and
said reagent is a colorimetric reagent.

3. The sensor of claim 2, wherein said polymer comprises a fluorinated ethylene sulfonic acid compound or derivative.

4. The sensor of claim 3, comprising signal-processing means for detecting the presence of at least one air constituent, wherein the presence of water vapor is deduced from an increase in the transmissivity of said waveguide.

5. The sensor of claim 4, wherein the presence of an acidic constituent is deduced from a change in the absorption of light of a selected wavelength range.

6. The sensor of claim 5, wherein said reagent comprises a pH indicator.

7. The sensor of claim 6, wherein said pH indicator comprises bromothymol blue or thymol blue.

8. The sensor of claim 7, wherein the selected wavelength range comprises the wavelength of 562 nm.

9. The sensor of claim 2 for the detection of basic air constituents, wherein said polymer comprises polyvinylpyrrolidone and said reagent comprises bromcresol green, said film having been first treated with acid so as to turn the reagent to its yellow form.

10. The sensor of claim 2, wherein said light-emitting diode and phototransistor are controlled by an electric circuit, said circuit causing the diode to be turned on and off in repetitive cycles.

11. The sensor of claim 1, wherein said film is disposed on a thin transparent substrate.

12. A sensor for detecting a selected air constituent comprising:
an optical waveguide having a front end and a rear end;
a light source for transmitting light of a selected wavelength to one end of the waveguide;
means for measuring the intensity of light emitted from the other end of the waveguide; and
signal-processing means for detecting the presence of at least one air constituent, wherein the presence of water vapor is deduced from an increase in the transmissivity of said waveguide and the presence of an acidic constituent is deduced from a change in the absorption of light of a selected wavelength range;

said waveguide comprising a film of material that comprises a reagent embedded in or forming part of a polymer;

said reagent yielding a substance having characteristic light-transmissive or light-adsorptive properties upon exposure to said air constituent;

wherein:
said light source is a light-emitting diode;
said photodetector is a phototransistor; and
said reagent is a colorimetric reagent;
said polymer comprises a fluorinated ethylene sulfonic acid compound or derivative; and
said reagent comprises a pH indicator;

wherein said signal-processing means includes means for distinguishing between the effects of water vapor and of acidic constituents.

13. The sensor of claim 12, wherein said distinguishing means comprises a second light-emitting diode whose range of emitted wavelengths is outside said light-absorption range.

14. The sensor of claim 13, wherein said distinguishing means comprises a timing circuit that causes the two diodes to go on and off in alternating cycles.

15. The sensor of claim 13, wherein said distinguishing means comprises a second waveguide and a second phototransistor operating in conjunction with the second diode.

16. The sensor of claim 13, wherein:
said pH-sensitive substance comprises bromothyl blue;
said light-absorption range comprises the wavelength of 562 nm; and
said second light-emitting diode emits at a wavelength of about 680 nm.

17. The sensor of claim 12, wherein said distinguishing means comprises a second waveguide and a second phototransistor, the film in said second waveguide being free of said pH indicator.

18. The sensor of claim 17, wherein said indicator is bromothymol blue or thymol blue.

19. A sensor for detecting a selected air constituent comprising:
an optical waveguide having a front end and a rear end;
a light source for transmitting light of a selected wavelength to one end of the waveguide; and
a photodetector for measuring the intensity of light emitted from the other end of the waveguide;
said waveguide comprising a film of material whose optical properties are susceptible to change in the presence of said air constituent;
wherein said film comprises a reagent embedded in or forming part of a polymer, said reagent yielding a substance having characteristic light-transmissive or light-absorptive properties upon exposure to said air constituent;
wherein said film is coating a substrate that is opaque to said selected wavelengths.

20. The sensor of claim 19, wherein said substrate comprises a rod that is opaque to said selected wavelengths and has two end surfaces and transparent lenses affixed onto each of said surfaces.

* * * * *